United States Patent
Xavier et al.

(10) Patent No.: US 11,660,260 B2
(45) Date of Patent: *May 30, 2023

(54) COMPOSITIONS AND METHODS FOR TREATING KERATINOUS SUBSTRATES

(71) Applicant: L'Oreal, Paris (FR)

(72) Inventors: Liliana Xavier, Mountainside, NJ (US); Anna Botto, Cranford, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/805,770

(22) Filed: Feb. 29, 2020

(65) Prior Publication Data

US 2021/0267868 A1 Sep. 2, 2021

(51) Int. Cl.
*A61K 8/46* (2006.01)
*A61K 8/37* (2006.01)
*A61Q 5/02* (2006.01)
*A61Q 19/10* (2006.01)
*A61Q 5/12* (2006.01)
*A61K 8/73* (2006.01)

(52) U.S. Cl.
CPC ............... *A61K 8/466* (2013.01); *A61K 8/37* (2013.01); *A61K 8/73* (2013.01); *A61Q 5/02* (2013.01); *A61Q 5/12* (2013.01); *A61Q 19/10* (2013.01)

(58) Field of Classification Search
CPC ... A61Q 5/02; A61Q 5/10; A61Q 5/12; A61Q 19/10; A61K 8/37; A61K 8/73; A61K 8/466

See application file for complete search history.

(56) References Cited

U.S. PATENT DOCUMENTS

| | | | |
|---|---|---|---|
| 7,183,245 B2 | 2/2007 | Moore | |
| 7,244,697 B2 | 7/2007 | Terada | |
| 8,790,627 B2 | 7/2014 | Erazo-Majewicz et al. | |
| 2006/0251601 A1 | 11/2006 | Arnaud | |
| 2009/0182046 A1* | 7/2009 | Dierker | A61K 9/0014 514/547 |
| 2016/0095804 A1* | 4/2016 | Xavier | A61K 8/44 510/127 |

FOREIGN PATENT DOCUMENTS

| | | |
|---|---|---|
| EP | 1690524 A2 | 8/2006 |
| EP | 1779845 A2 | 5/2007 |
| EP | 2020227 A1 | 2/2009 |
| GB | 2552566 A | 1/2018 |
| JP | 2017-214309 A | 12/2017 |
| KR | 10-2017-0061308 A | 6/2017 |
| WO | 2019/088455 A1 | 5/2019 |
| WO | 2019/232128 A1 | 12/2019 |
| WO | 2020/051118 A1 | 3/2020 |

OTHER PUBLICATIONS

Pink (unknown author), title: Safety Assessment of Alkyl Esters as Used in Cosmetics; Dec. 2012. (Year: 2012).*
International Search Report and Written Opinion for counterpart Application No. PCT/US2021/019333, dated Jun. 2, 2021.
Mintel: "Shampoo," K.M. Interlab, XP055807000, Database accession No. 7102413, Dec. 16, 2019.
Mintel: "Bath Gel," Sesderma, XP055807015, Database accession No. 4727597, Apr. 4, 2017.
Anonymous, "Ingredient Love-Coco Caprylate/Caprate—Ethique," XP055759025, Retrieved from the Internet: URL: https://salonsorbet.wordpress.com/2014/06/23/ingredient-love-coco-caprylatecaprate/ [retrieved on Dec. 10, 2020].
International Preliminary Report on Patentability and Written Opinion for counterpart Application No. PCT/US2021/019333, dated Sep. 6, 2022.
Mintel: "Thermal Finalizing De-Frizzing Cream," Tech-Science Cosmeticos, Record ID 630152, dated Dec. 2006.

* cited by examiner

*Primary Examiner* — Carlos A Azpuru
(74) *Attorney, Agent, or Firm* — The Marbury Law Group, PLLC

(57) ABSTRACT

Disclosed are conditioning systems comprising (a) at least one anionic surfactant chosen from isethionate surfactants; (b) coco-caprylate/caprate; and (c) at least one cationic compound, and rinse-off compositions comprising (a) an anionic surfactant system comprising i) a first anionic surfactant chosen from isethionate surfactants, and ii) optionally, a second anionic surfactant; (b) coco-caprylate/caprate; and (c) at least one cationic compound. Also disclosed are methods of treating and/or caring for the skin, hair, and/or scalp with the conditioning systems and/or rinse-off compositions containing the conditioning systems.

20 Claims, No Drawings

COMPOSITIONS AND METHODS FOR TREATING KERATINOUS SUBSTRATES

TECHNICAL FIELD

The disclosure relates to systems, compositions, and methods for treating keratinous substrates, such as skin, hair, and/or scalp. The compositions may be rinse-off compositions containing a conditioning system, such as a rinse-off conditioning shampoo or skin cleanser. The methods may comprise cleansing and/or conditioning the skin, hair, and/or scalp.

BACKGROUND

Individuals desire healthy skin and healthy, strong hair, as healthy-looking skin and hair is considered to be a sign of good health and good hygiene. Thus, cleansing the skin and hair is routine. However, traditional skin and hair cleansing compositions, while effective to cleanse the skin or hair, may deleteriously affect the appearance and/or condition of the skin or hair. For example, the skin may appear and feel dry, and hair gloss and moisture balance may be negatively affected making the hair more difficult to manage and style. Additionally, nutrition, environmental influences, and chemical treatments can lead to dry skin or hair damage that significantly weakens and dulls the hair over time. Furthermore, dry hair that has been weakened or damaged is also prone to breakage and the formation of "split ends."

In order to address these concerns, conditioning ingredients may be added to a skin cleansing or shampoo composition. However, such agents may negatively affect the properties of the composition itself. For example, addition of oils or esters may have negative effects on the foaming properties of the composition or may negatively affect the viscosity of the composition. Therefore, it is necessary to find the correct combination and amounts of conditioning agents for use in a skin or hair cleansing composition in order to provide excellent composition properties such as good foaming, lather, and distribution, while also imparting sufficient conditioning properties such as moisturized skin and/or detangling, shine, and smoothness to the hair.

The present disclosure addresses these concerns and relates to systems, compositions, and methods for treating the skin, hair, and/or scalp, such as with a rinse-off cleansing composition comprising a conditioning system which surprisingly exhibits both beneficial conditioning properties and superb composition properties.

SUMMARY

It has now been surprisingly and unexpectedly discovered that combining a particular anionic surfactant with a particular ester and a polysaccharide-based cationic compound provides an excellent conditioning system. The conditioning system may be included in a rinse-off skin or hair composition, such as, for example, a rinse-off skin cleanser or a shampoo composition.

According to various embodiments, the disclosure relates to rinse-off skin or hair compositions comprising (a) an anionic surfactant system comprising i) a first anionic surfactant chosen from isethionate surfactants, and ii) optionally, a second anionic surfactant; (b) coco-caprylate/caprate; (c) at least one cationic compound; (d) at least one additional surfactant chosen from non-ionic and amphoteric surfactants; and (e) water.

In further embodiments, the disclosure relates to rinse-off compositions comprising (a) an anionic surfactant system comprising i) from about 4% to about 15% by weight, relative to the total weight of the rinse-off composition, of a first anionic surfactant chosen from sodium cocoyl isethionate, sodium lauroyl isethionate, or a mixture thereof, and ii) at least one second anionic surfactant; (b) from about 0.01% to about 5% by weight, relative to the total weight of the rinse-off composition, of coco-caprylate/caprate; (c) at least one cationic compound chosen from at least one polysaccharide-based cationic compound, at least one cationic silicone compound, or a mixture thereof; (d) from about 7% to about 15% by weight, relative to the total weight of the rinse-off composition, of at least one alkypolyglucoside; (e) from about 0.01% to about 7% by weight, relative to the total weight of the rinse-off composition, of at least one amphoteric surfactant; and (f) water.

In yet further embodiments, the disclosure relates to a conditioning system comprising (a) at least one anionic surfactant chosen from isethionate surfactants, present in an amount ranging from about 90% to about 99% by weight, relative to the total weight of the conditioning system; (b) coco-caprylate/caprate, present in an amount ranging from about 0.5% to about 5% by weight, relative to the total weight of the conditioning system; and (c) at least one cationic compound, present in an amount ranging from about 0.5% to about 5% by weight, relative to the total weight of the conditioning system.

In still further embodiments relate to methods of cleansing and/or conditioning the skin, hair, and/or scalp comprising applying to the skin, hair, and/or scalp a composition comprising (a) an anionic surfactant system comprising i) a first anionic surfactant chosen from isethionate surfactants, and ii) optionally, a second anionic surfactant; (b) coco-caprylate/caprate; (c) at least one cationic compound; (d) at least one additional surfactant chosen from non-ionic and amphoteric surfactants; and (e) water.

DESCRIPTION

The disclosure relates, in various embodiments, to conditioning systems and rinse-off compositions containing the conditioning systems. The conditioning systems comprise: (a) at least one anionic surfactant chosen from isethionate surfactants; (b) coco-caprylate/caprate; and (c) at least one cationic compound. The rinse-off compositions comprise: (a) an anionic surfactant system comprising i) a first anionic surfactant chosen from isethionate surfactants, and ii) optionally, a second anionic surfactant; (b) coco-caprylate/caprate; and (c) at least one cationic compound. The disclosure also relates to methods of treating and/or caring for the skin, hair, and/or scalp with the conditioning systems and/or rinse-off compositions containing the conditioning systems, for example methods of cleansing and/or conditioning the skin, hair, and/or scalp.

Conditioning Systems

Conventional rinse-off cleansing compositions contain silicones or cationic polymers as their primary conditioning system. However, the present disclosure relates to new and surprisingly synergistic components for conditioning systems for use in rinse-off compositions, wherein the conditioning systems comprise: (a) at least one first anionic surfactant chosen from isethionate surfactants; (b) coco-caprylate/caprate; and (c) at least one cationic compound. The conditioning systems may be skin or hair conditioning systems, which may be used in any conventional skin or hair treatment and/or care composition, e.g. any conventional skin cleansing or shampoo composition.

Anionic Surfactant

The conditioning systems comprise at least one first anionic surfactant chosen from isethionate surfactants. According to various embodiments, the at least one isethionate surfactant may be chosen from acyl isethionates of the following formulae (I) or (II):

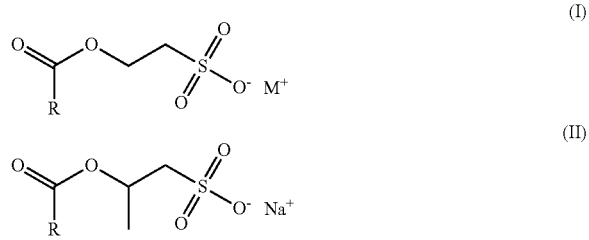

wherein R is chosen from H or an alkyl chain having from 1 to 30 carbon atoms, such as 6 to 24 carbon atoms, for example 8 to 20 carbon atoms, said chain being saturated or unsaturated, linear or branched, and $M^+$ is a cation. Although sodium is shown as the cation in formula (II), it should be understood that the cation for both formula (I) and formula (II) may be any alkali metal ion such as sodium or potassium, ammonium ions, or alkanolammonium ions such as monoethanolammonium or triethanolammonium ions.

By way of non-limiting example, suitable acyl isethionate surfactants may include the reaction product of fatty acids esterified with isethionic acid and neutralized with sodium hydroxide. For example, acyl isethionates surfactants may be prepared by the reaction of an isethionate salt such as a metal or ammonium isethionate and an a saturated or unsaturated, straight or branched, alkyl or alkenyl chain fatty acid having from 6 to 30 carbon atoms, preferably from 8 to 22 carbon atoms, more preferably from 6 to 18 carbon atoms. Optionally, a mixture of aliphatic fatty acids may be used for the preparation of commercial fatty acyl isethionates surfactants. Suitable fatty acids for isethionate surfactants can be derived from coconut oil or palm kernel oil, for instance.

Non-limiting examples of acyl isethionate surfactants that may be used include sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and mixtures thereof.

The total amount of isethionate surfactants may range up to about 15%, such as from about 4% to about 15% by weight, relative to the total weight of the rinse-off composition. For example, the total amount of isethionate surfactants may range from about 4% to about 14%, about 4% to about 13%, about 4% to about 12%, about 4% to about 11%, about 4% to about 10%, about 4% to about 9%, about 4% to about 8%, about 4% to about 7%, about 4% to about 6%, about 5% to about 15%, about 5% to about 14%, about 5% to about 13%, about 5% to about 12%, about 5% to about 11%, about 5% to about 10%, about 5% to about 9%, about 5% to about 8%, about 5% to about 7%, about 6% to about 15%, about 6% to about 14%, about 6% to about 13%, about 6% to about 12%, about 6% to about 11%, about 6% to about 10%, about 6% to about 9%, about 6% to about 8%, about 7% to about 15%, about 7% to about 14%, about 7% to about 13%, about 7% to about 12%, about 7% to about 11%, about 7% to about 10%, about 7% to about 9%, about 8% to about 15%, about 8% to about 14%, about 8% to about 13%, about 8% to about 12%, about 8% to about 11%, about 8% to about 10%, about 9% to about 15%, about 9% to about 14%, about 9% to about 13%, about 9% to about 12%, about 9% to about 11%, about 10% to about 15%, about 10% to about 14%, about 10% to about 13%, about 10% to about 12%, about 11% to about 15%, about 11% to about 14%, about 1% to about 13%, about 12% to about 15%, about 12% to about 14%, or about 13% to about 15% by weight, relative to the total weight of the rinse-off composition, including ranges and sub-ranges there between.

In various embodiments, the total amount of isethionate surfactants may range from about 90% to about 99.9%, by weight relative to the weight of the conditioning system. For example, the total amount of isethionate surfactants may range from about 91% to about 99%, such as about 92% to about 98%, about 93% to about 97%, or about 94% to about 96%, including all ranges and sub-ranges there between, by weight relative to the weight of the conditioning system. In various embodiments, the total amount of isethionate surfactants may be about 90%, about 91%, about 92%, about 93%, about 94%, about 95%, about 96%, about 97% about 98%, or about 99% by weight, relative to the total weight of the conditioning system.

Coco-Caprylate/Caprate

The conditioning system also comprises coco-caprylate, coco-caprate, or coco-caprylate/caprate, which is a blend of coco-caprylate and coco-caprate (collectively referred to as "coco-caprylate/caprate"). Coco-caprylate/caprate is a straight, unbranched wax ester made of C12-C18 coconut fatty alcohol and a blend of fractionated fatty acids of vegetable origin. By way of non-limiting example, the coco-caprylate/caprate product DUB™ 810C from the company Stéarinerie Dubois may be used.

In various embodiments, the amount of coco-caprylate/caprate may range up to about 5% by weight, relative to the total weight of the rinse-off composition. For example, the coco-caprylate/caprate may be present in the composition in an amount ranging from about 0.001% to about 5%, about 0.01% to about 4%, about 0.05% to about 3%, about 0.01% to about 2%, about 0.5% to about 2%, about 0.1% to about 2%, about 0.01% to about 1%, about 0.05% to about 1%, about 0.1% to about 1%, about 0.01% to about 0.5%, about 0.05% to about 0.5%, or about 0.1% to about 0.5%, including ranges and sub-ranges there between, by weight, relative to the total weight of the rinse-off composition. In various exemplary embodiments, the amount of the coco-caprylate/caprate may be about 0.01%, about 0.02%, about 0.03%, about 0.04%, 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 3.0%, about 3.5%, about 4.0%, about 4.5%, or about 5.0%, by weight, relative to the total weight of the rinse-off composition.

In various embodiments, the total amount of coco-caprylate/caprate may range from about 0.5% to about 5%, by weight relative to the weight of the conditioning system. For example, the total amount of coco-caprylate/caprate may range from about 1% to about 4%, such as about 1.5% to about 3.5%, about 1.75% to about 3.25%, or about 2% to about 3%, including all ranges and sub-ranges there between, by weight relative to the weight of the conditioning system. In various embodiments the total amount of coco-caprylate/caprate may be about 0.5%, about 0.75%, about 1%, about 1.25%, about 1.5%, about 1.75%, about 2%, about 2.25%, about 2.5% about 2.75%, about 3%, about 3.25%, about 3.5%, about 3.75%, about 4%, about 4.25%, about 4.5%, about 4.75%, or about 5% by weight, relative to the total weight of the conditioning system.

Cationic Compound

The conditioning system further comprises at least one cationic compound. Exemplary and non-limiting cationic compounds include cationic amine-based or quaternary ammonium-based compounds, cationic cellulose-based compounds, cationic starch-based compounds, cationic galactomannan compounds, and cationic silicone compounds.

In various exemplary embodiments, the at least one cationic compound may be chosen from cationic amine-based or quaternary ammonium-based compounds. By way of example, cationic amine-based compounds may be chosen from fatty amines, such as those comprising at least one C8-C30 hydrocarbon-based chain, for example a C12-C22 alkyl chain. As a non-limiting example, stearamidopropyl dimethylamine may be chosen.

Cationic quaternary ammonium-based compounds may be chosen from, for example, quaternary ammonium salts, such as compounds of formula (III):

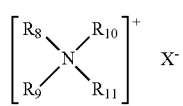

(III)

wherein:
R8 to R11, which may be identical or different, represent a linear or branched aliphatic group comprising from 1 to 30 carbon atoms, or an aromatic group such as aryl or alkylaryl, it being understood that at least one of the groups R8 to R11 comprises from 12 to 22 carbon atoms, and preferably from 16 to 22 carbon atoms; and X⁻ represents an organic or mineral anionic counterion, such as that chosen from halides, acetates, phosphates, nitrates, (C1-C4)alkyl sulfates, (C1-C4)alkyl- or (C1-C4)alkylaryl sulfonates.

Non-limiting examples of cationic quaternary ammonium based compounds include tetraalkylammonium salts, for instance dialkyldimethylammonium or alkyltrimethylammonium salts in which the alkyl group contains approximately from 16 to 22 carbon atoms, in particular behenyltrimethylammonium, distearyldimethyl-ammonium, cetyltrimethylammonium or benzyldimethylstearylammonium salts, or, on the other hand, the palmitylamidopropyltrimethylammonium salt, the stearamido-propyltrimethylammonium salt, the stearamidopropyldimethylcetearylammonium salt, or the stearamidopropyldimethyl(myristyl acetate)ammonium salt, behentrimonium chloride, cetrimonium chloride, and behentrimonium methosulfate.

In further exemplary embodiments, the cationic compound may be a polysaccharide-based cationic compound, for example may be chosen from cationic cellulose derivatives such as those available from Amerchol Corp. (Edison, N.J., USA) in their Polymer JR™ and LR™ series of polymers, as salts of hydroxyethyl cellulose reacted with trimethyl ammonium substituted epoxide (referred to as Polyquaternium-10); polymeric quaternary ammonium salts of hydroxyethyl cellulose reacted with lauryl dimethyl ammonium-substituted epoxide (referred to as Polyquaternium-24), available from Amerchol Corp. under the tradename Polymer LM-200; or Polyquaternium-67 (quaternized hydroxyethyl cellulose), such as the product SOFTCAT® POLYMER SL 100 sold by the company Dow Chemical.

Other exemplary cationic Polyquaternium compounds useful according to the disclosure include, but are not limited to, Polyquaternium-1 (ethanol, 2,2',2"-nitrilotris-, polymer with 1,4-dichloro-2-butene and N,N,N',N'-tetramethyl-2-butene-1,4-diamine); Polyquaternium-2, (poly[bis (2-chloroethyl) ether-alt-1,3-bis[3-(dimethylamino)propyl] urea]); Polyquaternium-4, (hydroxyethyl cellulose dimethyl diallylammonium chloride copolymer; Diallyldimethylammonium chloride-hydroxyethyl cellulose copolymer); Polyquaternium-5 (copolymer of acrylamide and quaternized dimethylammoniumethyl methacrylate); Polyquaternium-6 (poly(diallyldimethylammonium chloride)); Polyquaternium-7 (copolymer of acrylamide and diallyldimethylammonium chloride); Polyquaternium-8 (copolymer of methyl and stearyl dimethylaminoethyl ester of methacrylic acid, quaternized with dimethylsulphate); Polyquaternium-9 (homopolymer of N,N-(dimethylamino)ethyl ester of methacrylic acid, quaternized with bromomethane); Polyquaternium-11 (copolymer of vinylpyrrolidone and quaternized dimethylaminoethyl methacrylate); Polyquaternium-12 (ethyl methacrylate/abietyl methacrylate/diethylaminoethyl methacrylate copolymer quaternized with dimethyl sulfate); Polyquaternium-13 (ethyl methacrylate/oleyl methacrylate/diethylaminoethyl methacrylate copolymer quaternized with dimethyl sulfate); Polyquaternium-14 (trimethylaminoethylmethacrylate homopolymer); Polyquaternium-15 (acrylamide-dimethylaminoethyl methacrylate methyl chloride copolymer); Polyquaternium-16 (copolymer of vinylpyrrolidone and quaternized vinylimidazole); Polyquaternium-17 (adipic acid, dimethylaminopropylamine and dichloroethylether copolymer); Polyquaternium-18 (azelanic acid, dimethylaminopropylamine and dichloroethylether copolymer); Polyquaternium-19 (copolymer of polyvinyl alcohol and 2,3-epoxypropylamine); Polyquaternium-20 (copolymer of polyvinyl octadecyl ether and 2,3-epoxypropylamine); Polyquaternium-22 (copolymer of acrylic acid and diallyldimethylammonium chloride); Polyquaternium-27 (block copolymer of Polyquaternium-2 and Polyquaternium-17); Polyquaternium-28 (copolymer of vinylpyrrolidone and methacrylamidopropyl trimethylammonium); Polyquaternium-29 (chitosan modified with propylen oxide and quaternized with epichlorhydrin); Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate); Polyquaternium-31 (N,N-dimethylaminopropyl-N-acrylamidine quaternized with diethylsulfate bound to a block of polyacrylonitrile); Polyquaternium-32 (poly(acrylamide 2-methacryloxyethyltrimethyl ammonium chloride)); Polyquaternium-33 (copolymer of trimethylaminoethylacrylate salt and acrylamide); Polyquaternium-34 (copolymer of 1,3-dibromopropane and N,N-diethyl-N',N'-dimethyl-1,3-propanediamine); Polyquaternium-35 (methosulphate of the copolymer of methacryloyloxyethyltrimethylammonium and of methacryloyloxyethyldimethylacetyl-ammonium); Polyquaternium-36 (copolymer of N,N-dimethylaminoethylmethacrylate and butylmethacrylate, quaternized with dimethylsulphate); Polyquaternium-37 (poly(2-methacryloxyethyltrimethylammonium chloride)); Polyquaternium-39 (terpolymer of acrylic acid, acrylamide and diallyldimethylammonium Chloride); Polyquaternium-42 (poly[oxyethylene(dimethylimino)ethylene (dimethylimino)ethylene dichloride]); Polyquaternium-43 (copolymer of acrylamide, acrylamidopropyltrimonium chloride, 2-amidopropylacrylamide sulfonate and dimethylaminopropylamine); Polyquaternium-44 (3-Methyl-1-vinylimidazolium methyl sulfate-N-vinylpyrrolidone copolymer); Polyquaternium-45 (copolymer of (N-methyl-N-ethoxyglycine)methacrylate and N,N-dimethylaminoethylmethacrylate, quaternized with dimethyl sulphate); Polyquaternium-46 (terpolymer of vinylcaprolactam, vinylpyrrolidone, and quaternized vinylimidazole); Polyquaternium-47 (terpolymer of acrylic acid, methacrylamidopropyl trimethylammonium chloride, and methyl acrylate); and Polyquaternium-53 (terpolymer of acrylic acid/maptac/acrylamide).

In yet further exemplary embodiments, the cationic compound may be chosen from cationic galactomannan compounds, such as cationic guar-based compounds. For example, compounds such as guar gums containing trialkylammonium cationic groups may be chosen. Exemplary and non-limiting useful cationic guar gum compounds are those given the designation of guar hydroxypropyl trimonium chloride, available commercially for example as JAGUAR® C13S, which has a low degree of substitution of the cationic groups and a high viscosity. Other exemplary and non-limiting useful materials include that known as JAGUAR® C15, having a moderate degree of substitution and a low viscosity, JAGUAR® C17, and JAGUAR® C16 which is a hydroxypropylated cationic guar derivative containing a low level of substituent groups as well as cationic quaternary ammonium groups. Guar hydroxypropyl trimonium chloride may also be available commercially for example as N-HANCE CG13 from the company Ashland. Also useful is hydroxypropyl guar hydroxypropyltrimonium chloride, commercially available as JAGUAR® 162.

In yet further embodiments, cationic silicone compounds, for example amino silicones, may be chosen. As used herein, the term "amino silicone" means any polyaminosiloxane, e.g. any polysiloxane comprising at least one primary, secondary or tertiary amine function or a quaternary ammonium group. By way of example, compounds of formula (IV) may be chosen:

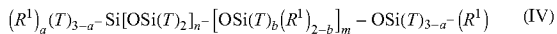

wherein:
T is a hydrogen atom or a phenyl, hydroxyl (—OH) or C1-C8 alkyl radical, and preferably methyl, or a C1-C8 alkoxy, preferably methoxy;
a denotes the number 0 or an integer from 1 to 3, and preferably 0;
b denotes 0 or 1, preferably 1;
m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;
R1 is a monovalent radical of formula —CqH2qL in which q is a number from 2 to 8 and L is an optionally quaternized amino group selected from the following groups: N(R2)-CH2-CH2-N(R2)2; N(R2)2; N(R2)3Q–; N+(R2)(H)2Q–; N+(R2)2HQ–; N(R2)-CH2-CH2-N+(R2)(H)2Q–; and
R2 denotes a hydrogen atom, a phenyl, a benzyl or a saturated monovalent hydrocarbon-based radical, for example a C1-C20 alkyl radical; and
Q– represents a halide ion, for instance fluoride, chloride, bromide or iodide.

By way of example, trimethylsilylamodimethicone may be chosen.

In a further example, cationic amino silicones may be chosen from those of formula (V):

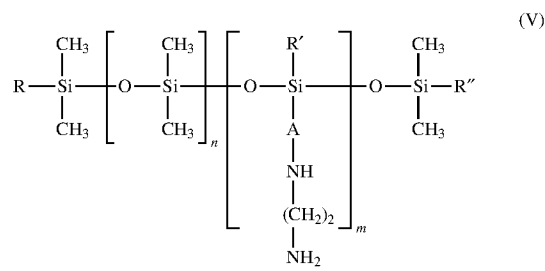

wherein:
R, R' and R", which may be identical or different, denote a C1-C4 alkyl radical, preferably CH3; a C1-C4 alkoxy radical, preferably methoxy; or —OH;
A represents a linear or branched, C3-C8 and preferably C3-C6 alkylene radical; and
m and n are integers dependent on the molecular weight and whose sum is between 1 and 2000.

In one embodiment, in formula (V), R, R', R", which may be identical or different, represent a C1-C4 alkyl or hydroxyl radical, A represents a C3 alkylene radical and m and n are such that the weight-average molecular weight of the compound is between about 5000 and 500,000. Compounds of this type are referred to as "aminodimethicones".

In a further embodiment, in formula (V), R, R' and R", which may be identical or different, represent a C1-C4 alkoxy or hydroxyl radical, at least one of the radicals R or R" is an alkoxy radical and A represents a C3 alkylene radical. The hydroxy/alkoxy molar ratio may be between 0.2/1 and 0.4/1, for example equal to 0.3/1. Moreover, m and n are such that the weight-average molecular weight of the compound is between about 2000 and 10$^6$. More particularly, n is between 0 and 999 and m is between 1 and 1000, the sum of n and m being between 1 and 1000. For example, the product BELSIL® ADM 652 sold by Wacker may be chosen.

In yet a further embodiment, in formula (V) R and R", which are different, represent a C1-C4 alkoxy or hydroxyl radical, at least one of the radicals R or R" is an alkoxy radical, R' represents a methyl radical, and A represents a C3 alkylene radical. The hydroxy/alkoxy molar ratio is preferably between 1/0.8 and 1/1.1, for example equal to 1/0.95. Moreover, m and n are such that the weight-average molecular weight of the compound is between about 2000 and 200,000. More particularly, n is between 0 and 999 and m is between 1 and 1000, the sum of n and m being between 1 and 1000. For example, the product FLUID WR® 1300 sold by Wacker may be chosen.

In a still further embodiment, in formula (V) R and R" represent a hydroxyl radical, R' represents a methyl radical, and A is a C4-C8, preferably C4, alkylene radical. Moreover, m and n are such that the weight-average molecular weight of the compound is between about 2000 and $10^6$. More particularly, n is between 0 and 1999 and m is between 1 and 2000, the sum of n and m being between 1 and 2000. For example, the product DC 28299 by Dow Corning may be chosen.

The at least one cationic compound may be present in the composition in an amount ranging up to about 5% by weight, relative to the total weight of the rinse-off composition. For example, the at least one cationic compound may be present in the rinse-off composition in an amount ranging from about 0.001% to about 5%, about 0.01% to about 4%, about 0.05% to about 3%, about 0.01% to about 2%, about 0.5% to about 2%, about 0.1% to about 2%, about 0.01% to about 1%, about 0.05% to about 1%, about 0.1% to about 1%, about 0.01% to about 0.5%, about 0.05% to about 0.5%, or about 0.1% to about 0.5%, including ranges and sub-ranges there between, by weight, relative to the total weight of the composition. In various exemplary embodiments, the amount of the at least one cationic compound may be about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 3.0%, about 3.5%, about 4.0%, about 4.5%, or about 5.0%, by weight, relative to the total weight of the rinse-off composition.

In various embodiments, the total amount of the cationic compound may range from about 0.5% to about 5%, by weight relative to the weight of the conditioning system. For example, the total amount of the polysaccharide-based cationic compound may range from about 1% to about 4%, such as about 1.5% to about 3.5%, about 1.75% to about 3.25%, about 1.75% to about 2.75%, or about 2% to about 3%, including all ranges and sub-ranges there between, by weight relative to the weight of the conditioning system. In various embodiments the total amount of the cationic compound may be about 0.5%, about 0.75%, about 1%, about 1.25%, about 1.5%, about 1.75%, about 2%, about 2.25%, about 2.5% about 2.75%, about 3%, about 3.25%, about 3.5%, about 3.75%, about 4%, about 4.25%, about 4.5%, about 4.75%, or about 5% by weight, relative to the total weight of the conditioning system.

Rinse-Off Compositions

The conditioning systems according to the disclosure may be incorporated into or included in a rinse-off skin or hair composition. For example, the rinse-off composition may be a skin-cleansing composition or a shampoo composition, such as a conditioning shampoo composition. Accordingly, the rinse-off compositions may comprise components that are traditional or useful in such compositions, in addition to the components of the conditioning system.

Anionic Surfactant System

When the conditioning system is incorporated into a rinse-off composition, the composition may optionally comprise at least one second anionic surfactant, in addition to the one or more isethionate(s) of the conditioning system. The combination of the one or more isethionate(s) with the second anionic surfactant(s) makes up the anionic surfactant system. As used herein, the term "anionic surfactant" means a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$, $O_2PO_2H$, $O_2PO_2H$, and $O_2PO_2^{2-}$.

When present, the at least one second anionic surfactant may be chosen from either non-sulfate or sulfate-based anionic surfactants.

In one embodiment, the composition is free or substantially free of sulfate-based surfactants. If present, sulfate-based anionic surfactants may be chosen from, for example, alkyl sulfates, alkyl ether sulfates, alkylamido ether sulfates, alkylaryl polyether sulfates, monoglyceride sulfates, or mixtures thereof. In various embodiments, the anionic surfactant may be chosen from $(C_6-C_{24})$alkyl sulfates, $(C_6-C_{24})$alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. More preferentially, the anionic surfactant(s) are chosen from $(C_{10}-C_{20})$alkyl ether sulfates, and in particular sodium lauryl ether sulfate, optionally containing 2.2 mol of ethylene oxide. In other embodiments, sodium lauryl sulfate, sodium lauryl ether sulfate, ammonium lauryl sulfate, ammonium lauryl ether sulfate, sodium laureth sulfate, or mixtures thereof may be chosen.

In various exemplary embodiments, the anionic surfactant system comprises at least one second anionic surfactant chosen from non-sulfate anionic surfactants, such as, for example, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

Useful alkyl sulfonates include those of formula (VI):

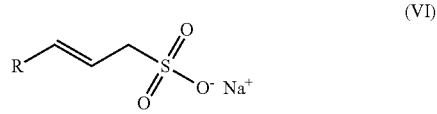

(VI)

wherein R is selected from H or alkyl chain that has from 1 to 30 carbon atoms, such as from 6 to 24 carbon atoms, for example from 8 to 20 carbon atoms, said chain being saturated or unsaturated, linear or branched. It should be noted that although sodium is shown as the cation in the above formula (VI), the cation may be any alkali metal ion such as sodium or potassium, ammonium ions, or alkanolammonium ions such as monoethanolammonium or triethanolammonium ions. In some instances, the alkyl sulfonate(s) are selected from C8-C16 alkyl benzene sulfonates, C10-C20 paraffin sulfonates, C10-C24 olefin sulfonates, salts thereof, and mixtures thereof.

By way of non-limiting example, alkyl sulfonates may be chosen from alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkane-sulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

Non-limiting examples of useful alkyl sulfosuccinates include those of formula (VII):

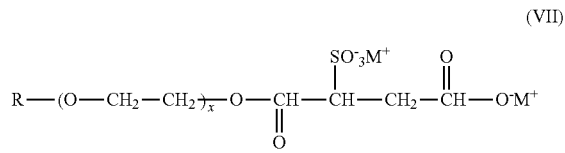

(VII)

wherein R is a straight or branched chain alkyl or alkenyl group having from 10 to 22 carbon atoms, such as 10 to 20 carbon atoms, and $M^+$ is a cation which can independently of each other be, for example, any alkali metal ion such as sodium, potassium, or ammonium, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a mixture thereof.

Exemplary and non-limiting alkyl sulfoacetates include C4-C18 fatty alcohol sulfoacetates and/or salts thereof, such as sodium lauryl sulfoacetate. Useful cations for the salts include any alkali metal ion such as sodium or potassium, ammonium ions, or alkanolammonium ions such as monoethanolammonium or triethanolammonium ions.

Non-limiting examples of alkoxylated monoacids include compounds corresponding to formula (VIII):

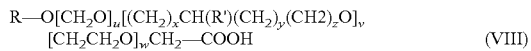

(VIII)

wherein:
R is a hydrocarbon radical containing from about 6 to about 40 carbon atoms;
u, v, and w, independently of one another, represent numbers of from 0 to 60;
x, y, and z, independently of one another, represent numbers of from 0 to 13;
R' represents hydrogen or alkyl; and
the sum of x+y+z>0.

Compounds corresponding to formula (VIII) may be obtained by alkoxylation of alcohols R—OH with ethylene oxide as the sole alkoxide, or with several alkoxides and subsequent oxidation. The numbers u, v, and w each represent the degree of alkoxylation. Whereas, on a molecular level, the numbers u, v, and w and the total degree of alkoxylation can only be integers, including zero, on a macroscopic level they are mean values in the form of broken numbers.

In formula (VIII), R is linear or branched, acyclic or cyclic, saturated or unsaturated, aliphatic or aromatic, substituted or unsubstituted. R may be a linear or branched, acyclic C6-40 alkyl or alkenyl group, or a C1-40 alkyl phenyl group, for example a C8-22 alkyl or alkenyl group or a C4-18 alkyl phenyl group, such as a C12-18 alkyl group or alkenyl group or a C6-16 alkyl phenyl group; u, v, w, independently of one another, may be a number from 2 to 20, for example a number from 3 to 17, such as a number from 5 to 15; x, y, z, independently of one another, may be a number from 2 to 13, for example a number from 1 to 10, such as a number from 0 to 8.

By way of example only, useful alkoxylated monoacids include Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof. In some cases, preferred ethoxylated acids include Oleth-10 Carboxylic Acid, Laureth-5 Carboxylic Acid, Laureth-11 Carboxylic Acid, and mixtures thereof.

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of useful acyl amino acids include those of formula (IX):

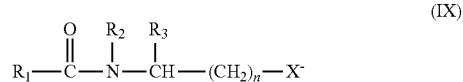

(IX)

wherein R, R1, R2, and R3 are each independently selected from H or an alkyl chain having from 1 to 30 carbon atoms, said chain being saturated or unsaturated, linear or branched, and X is $COO^-$ or $SO_3^-$.

By way of example, useful acyl amino acids include acyl taurates, acyl glycinates, acyl glutamates, acyl sarcosinates, salts thereof, and mixtures thereof.

Exemplary useful acyl taurates include those of formula (X):

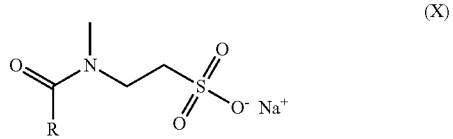

(X)

wherein R is selected from H or an alkyl chain having from 1 to 30 carbon atoms, such as from 6 to 24 carbon atoms, for example from 8 to 20 carbon atoms, said chain being saturated or unsaturated, linear or branched. It should be noted that although sodium is shown as the cation in the above formula (X), the cation may be any alkali metal ion such as sodium or potassium, ammonium ions, or alkanolammonium ions such as monoethanolammonium or triethanolammonium ions. Non-limiting examples of acyl taurate salts include sodium cocoyl taurate, sodium methyl cocoyl taurate, and mixtures thereof.

Exemplary useful acyl glycinates include those of formula (XI):

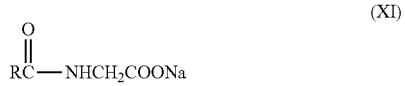

(XI)

wherein R is an alkyl chain of 8 to 16 carbon atoms. It should be noted that although sodium is shown as the cation in the above formula (XI), the cation may be any alkali metal ion such as sodium, potassium, or ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and mixtures thereof.

Exemplary useful acyl glutamates include those of formula (XII):

(XII)

wherein R is an alkyl chain of 8 to 16 carbon atoms. It should be noted that although sodium is shown as the cation in the above formula (XII), the cation may be any alkali metal ion such as sodium, potassium, or ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, disodium cocoyl glutamate, and mixtures thereof.

Non-limiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, ammonium lauroyl sarcosinate, and mixtures thereof.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt. Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used. Exemplary salts of $C_6$-$C_{24}$ alkyl monoesters of polyglycoside-polycarboxylic acids include $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

The anionic surfactant system may be present in the rinse-off composition in an amount ranging from about 5% to about 25%, by weight, relative to the total weight of the composition. For example, the anionic surfactant system may be present in an amount ranging from about 5% to about 24%, about 5% to about 23%, about 5% to about 22%, about 5% to about 21%, about 5% to about 20%, about 6% to about 25%, about 6% to about 24%, about 6% to about 23%, about 6% to about 22%, about 6% to about 21%, about 6% to about 20%, about 7% to about 25%, about 7% to about 24%, about 7% to about 23%, about 7% to about 22%, about 7% to about 21%, about 7% to about 20%, about 8% to about 25%, about 8% to about 24%, about 8% to about 23%, about 8% to about 22%, about 8% to about 21%, about 8% to about 20%, about 9% to about 25%, about 9% to about 24%, about 9% to about 23%, about 9% to about 22%, about 9% to about 21%, about 9% to about 20%, about 10% to about 25%, about 10% to about 24%, about 10% to about 23%, about 10% to about 22%, about 10% to about 21%, or about 10% to about 20%, including ranges and sub-ranges there between, by weight, based on the weight of the total composition.

The amount of the at least one second anionic surfactant, if present, will be chosen such that the total anionic surfactant system is present in the rinse-off composition in the amounts described above, taking into consideration the amount of the first anionic surfactant chosen from isethionates.

Other Surfactants

Optionally, the rinse-off composition may comprise other surfactants in addition to those of the anionic surfactant system. By way of example, the rinse-off compositions may comprise non-ionic and/or amphoteric surfactants.

As exemplary and non-limiting non-ionic surfactants, alkyl polyglucosides and/or monounsaturated glyceryl esters may be chosen.

In certain embodiments, the rinse-off composition comprises at least one alkyl polyglucoside having the following formula (XIII):

(XIII)

wherein:

$R^1$ is an alkyl group having from 8 to 18 carbon atoms;
$R^2$ is an ethylene or propylene group;
Z is a saccharide group with 5 to 6 carbon atoms;
n is an integer from 0 to 10; and
x is an integer from 1 to 5.

Nonlimiting examples of alkyl polyglucosides include lauryl glucoside, octyl glucoside, decyl glucoside, coco glucoside, caprylyl/capryl glucoside, and sodium lauryl glucose carboxylate. In certain embodiments, the at least one alkyl poly glucoside compound is selected from the group consisting of lauryl glucoside, decyl glucoside, coco glucoside, and mixtures thereof.

The total amount of alkyl polyglucosides in the rinse-off compositions may vary, but typically ranges from about 0.01% to about 15%, such as about 0.1% to about 15%, or about 1% to about 15% by weight, based on the total weight of the composition. For example, the total amount of alkyl polyglucosides may range from about 5% to about 15%, from about 6% to about 14%, from about 7% to about 13%, from about 7% to about 12%, from about 8% to about 12%, from about 9% to about 12%, or from about 10% to about 12%, including ranges and sub-ranges there between, by weight based on the total weight of the rinse-off composition. In various non-limiting embodiments, the total amount of alkyl polyglucosides is about 5%, about 6%, about 7%, about 8%, about 9%, about 10%, about 11%, about 12%, about 13%, about 14%, or about 15%, by weight based on the total weight of the rinse-off composition.

In certain embodiments, the rinse-off composition may comprise monounsaturated glyceryl esters such as, for example, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, or mixtures thereof. In certain embodiments, the at least one monounsaturated glyceryl ester may be chosen from polyglyceryl-4 isostearate, polyglyceryl-3 oleate, polyglyceryl-2 sesquioleate, triglyceryl diisostearate, diglyceryl monooleate, tetraglyceryl monooleate, or mixtures thereof.

Optionally, the rinse-off composition may further comprise at least one amphoteric surfactant. Non-limiting examples of amphoteric surfactants include betaines, sultaines, amphoacetates, amphoprorionates, and mixtures thereof. In certain embodiments, betaines and amphoprorionates are used. In certain embodiments, betaines are used. Betaines which can be used in the current compositions include those having the following formulae (XIV)-(XVII):

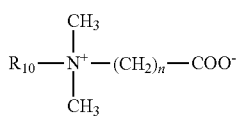

(XIV)

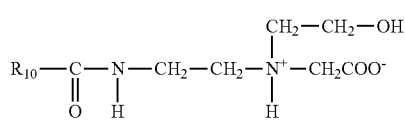

(XV)

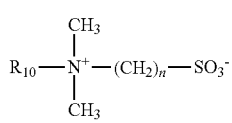

(XVI)

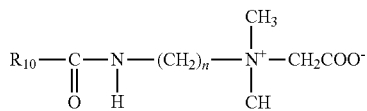

(XVII)

wherein in formulae (XIV)-(XVII):
R10 is an alkyl group having from 8 to 18 carbon atoms; and
n is a integer from 1 to 3.

Non-limiting examples of betaines include coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. In certain embodiments, the at least one betaine compound may be chosen from the group consisting of coco betaine, cocoamidopropyl betaine, behenyl betaine, capryl/capramidopropyl betaine, lauryl betaine, and mixtures thereof.

Hydroxyl sultaines useful in the compositions according to embodiments of the disclosure include the following formula (XVIII):

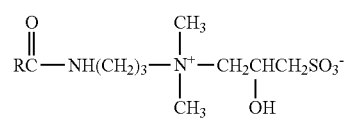

(XVIII)

wherein R is an alkyl group having from 8 to 18 carbon atoms.

Useful alkylamphoacetates include those having the formula (XIX):

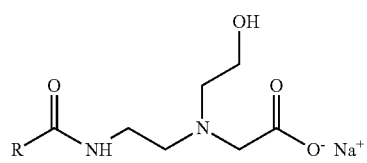

(XIX)

wherein R is an alkyl group having from 8 to 18 carbon atoms.

Useful alkyl amphodiacetates include those having the formula (XX):

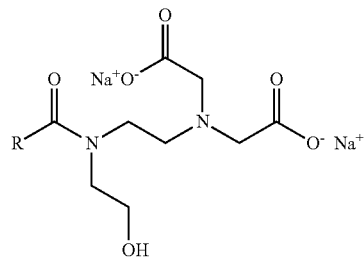

(XX)

wherein R is an alkyl group having from 8 to 18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of $(C_8-C_{20})$alkylbetaines, $(C_8-C_{20})$alkylamido $(C_1-C_6)$alkylbetaines, sulfobetaines, $(C_8-C_{20})$alkylsulfobetaines, $(C_8-C_{20})$alkylamido $(C_1-C_8)$alkylsulfobetaines, $(C_8-C_{20})$alkylamphoacetate, $(C_8-C_{20})$alkylamphodiacetate, and mixtures thereof.

Among the optionally quaternized secondary or tertiary aliphatic amine derivatives that may be used, mention may also be made of the products of respective structures (A1) and (A2) below:

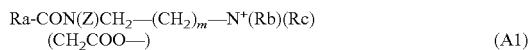

wherein:
Ra represents a $C_{10}-C_{30}$ alkyl or alkenyl group derived from an acid Ra-COOH preferably present in hydrolysed coconut oil, a heptyl group, a nonyl group or an undecyl group,
Rb represents a β-hydroxyethyl group,
Rc represents a carboxymethyl group;
m is equal to 0, 1 or 2, and
Z represents a hydrogen atom or a hydroxyethyl or carboxymethyl group;

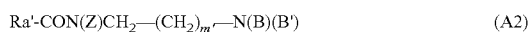

wherein:
B represents —CH$_2$CH$_2$OX', with X' representing —CH$_2$—COOH, CH$_2$—COOZ', CH$_2$CH$_2$—COOH, —CH$_2$CH$_2$—COOZ', or a hydrogen atom,
B' represents —(CH$_2$)$_z$—Y', with z=1 or 2, and Y' representing COOH, COOZ', CH$_2$—CHOH—SO$_3$H or —CH$_2$—CHOH—SO$_3$Z',
m' is equal to 0, 1 or 2,
Z represents a hydrogen atom or a hydroxyethyl or carboxymethyl group,
Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris (hydroxymethyl)aminomethane, and
Ra' represents a $C_{10}-C_{30}$ alkyl or alkenyl group of an acid Ra'COOH preferably pre-sent in hydrolysed linseed oil or coconut oil, an alkyl group, in particular a $C_{17}$ alkyl group, and its iso form, or an unsaturated $C_{17}$ group.

Exemplary amphoteric surfactants include sodium cocoamphoacetate, sodium lauroamphoacetate, sodium caproamphoacetate and sodium capryloamphoacetate. Further exemplary amphoteric surfactants include disodium cocoamphodiacetate, disodium lauroamphodiacetate, disodium caproamphodiacetate, disodium capryloamphodiacetate, disodium cocoamphodi-propionate, disodium lauroamphodipropionate, disodium caproamphodipropionate, disodium capryloamphodi-propionate, lauroamphodipropionic acid and coco-amphodipropionic acid.

Non-limiting examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (XXI):

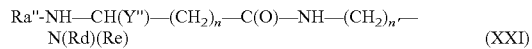

wherein:
Ra" represents a C10-C30 alkyl or alkenyl group of an acid Ra"—C(O)OH preferably present in hydrolysed linseed oil or coconut oil;
Y" represents the group —C(O)OH, —C(O)OZ", —CH$_2$—CH(OH)—SO$_3$H or the group CH$_2$—CH (OH)—SO$_3$—Z", with Z" representing a cationic counterion resulting from an alkali metal or alkaline-earth metal, such as sodium, an ammonium ion or an ion resulting from an organic amine;
Rd and Re represent, independently of each other, a $C_1-C_4$ alkyl or hydroxyalkyl radical; and
n and n' denote, independently of each other, an integer ranging from 1 to 3.

Exemplary compounds include sodium diethylaminopropylcoco-aspartamide, such as the one sold by the company Chimex under the name CHIMEXANE HB.

In certain embodiments, the amphoteric surfactants are chosen from $(C_8-C_{20})$alkylbetaines, $(C_8-C_{20})$alkylamido $(C_1-C_8)$alkylbetaines, $(C_8-C_{20})$alkylamphoacetates and $(C_8-C_{20})$alkylamphodiacetates, and mixtures thereof.

In certain embodiments, the at least one amphoteric surfactant is chosen from $(C_8-C_{20})$alkyl betaines, $(C_8-C_{20})$ alkylamido $(C_1-C_6)$alkylbetaines, $(C_8-C_{20})$alkylamphoacetate, $(C_8-C_{20})$alkylamphodiacetate, and their salts, and mixtures thereof. In some cases, the at least one amphoteric surfactant is selected from coco-betaine, cocamidopropylbetaine, sodium cocoamphoacetate, disodium cocoamphodiacetate, and mixtures thereof.

The amphoteric surfactant may be present in an amount up to about 10%, such as about 0.001% to about 10%, or about 0.001% to about 5% by weight, relative to the total weight of the rinse-off composition. For example, the amphoteric surfactant may be present in the rinse-off composition in an amount ranging from about 0.001% to about 3%, about 0.01% to about 3%, about 0.05% to about 3%, about 0.1% to about 3%, about 1% to about 3%, about 1.5% to about 3%, about 2% to about 3%, about 2.5% to about 3%, about 0.01% to about 2%, about 0.05% to about 2%, about 0.1% to about 2%, about 0.01% to about 1%, about 0.05% to about 1%, about 0.1% to about 1%, or about 0.05% to about 0.5%, including ranges and sub-ranges there between, by weight, relative to the total weight of the composition. In various exemplary embodiments, the amount of the amphoteric surfactant may be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% by weight, relative to the total weight of the rinse-off composition.

Emulsifiers

The rinse-off compositions according to the disclosure may optionally comprise one or more emulsifiers. In various embodiments, the emulsifiers may be chosen from fatty acids, fatty alcohols, esters of polyols and of a fatty acid, polyol fatty esters and fatty ethers with a branched or unsaturated chain containing from 10 to 30 carbon atoms, esters of sugar and of a fatty acid, and a mixture thereof. Nonlimiting examples of emulsifiers include ricinoleic acid, glycerol monostearate, glycol distearate, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, PEG-150 distearate, or mixtures thereof.

Cosmetically Acceptable Solvent

The rinse-off compositions according to the disclosure comprise at least one cosmetically acceptable solvent. In certain embodiments, the cosmetically acceptable solvents may be chosen from organic solvents, water-soluble solvents, water, or mixtures thereof.

The total amount of cosmetically acceptable solvent in the rinse-off compositions may vary, but is typically from about 25% to about 95%, based on the total weight of the rinse-off compositions. In some cases, the total amount of water is about 30% to about 90%, about 35% to about 85%, about 40% to about 75%, about 45% to about 70%, or about 50% to about 65%, including ranges and sub-ranges there between, by weight based on the total weight of the rinse-off composition.

Additional Components

In various embodiments, it may be advantageous to include additional components in the rinse-off compositions according to the disclosure. By way of non-limiting example, it may be advantageous to include at least one carboxylic acid, such as at least one organic compound that includes one, two, three, or more carboxylic acid functional groups (—COOH) and at least one carbon atom. Exemplary and non-limiting carboxylic acids may include oxalic acid, malonic acid, malic acid, glutaric acid, citraconic acid, citric acid, maleic acid, glycolic acid, succinic acid, adipic acid, tartaric acid, fumaric acid, sebacic acid, benzoic acid, and glyoxylic acid monohydrate, as well as combinations thereof.

If present, the at least one carboxylic acid may be present in an amount up to about 5% by weight, relative to the weight of the rinse-off composition. For example, the at least one carboxylic acid may be present in the rinse-off composition in an amount ranging from about 0.001% to about 5%, about 0.01% to about 4%, about 0.05% to about 3%, about 0.01% to about 2%, about 0.5% to about 2%, about 0.1% to about 2%, about 0.01% to about 1.5%, about 0.05% to about 1.5%, about 0.1% to about 1.5%, about 0.01% to about 1%, about 0.05% to about 1%, or about 0.1% to about 1%, including ranges and sub-ranges there between, by weight, relative to the total weight of the composition. In various exemplary embodiments, the amount of the at least one carboxylic acid may be about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 3.0%, about 3.5%, about 4.0%, about 4.5%, or about 5.0%, by weight, relative to the total weight of the rinse-off composition.

In further embodiments, the rinse-off composition may optionally comprise at least one ethanolamine compound. By way of example only, the composition may comprise monoethanolamine (MEA), diethanolamine (DEA), triethanolamine (TEA), or a mixture thereof. If present, the at least one ethanolamine may range up to about 2%, such as up to about 1.5%, up to about 1%, up to about 0.5%, or up to about 0.1% by weight, such as about 0.01%, relative to the total weight of the rinse-off composition. For example, the ethanolamine may be present in the rinse-off composition in an amount ranging from about 0.001% to about 2%, about 0.01% to about 2%, about 0.05% to about 2%, about 0.1% to about 2%, about 0.001% to about 1%, about 0.01% to about 1%, about 0.05% to about 1%, about 0.1% to about 1%, about 0.001% to about 0.5%, about 0.01% to about 0.5%, about 0.05% to about 0.5%, or about 0.1% to about 0.5%, including ranges and sub-ranges there between, by weight, relative to the total weight of the composition.

The compositions in certain embodiments may also optionally comprise stabilizers, for example sodium chloride, magnesium dichloride or magnesium sulfate.

The rinse-off composition according to the disclosure may also comprise further additives chosen from nacreous agents, dyes or pigments, fragrances, mineral, plant or synthetic oils, waxes, vitamins (e.g. panthenol, Vitamin E, biotin, etc.), proteins including ceramides, vitamins, UV-screening agents, free-radical scavengers, antidandruff agents, hair-loss counteractants, hair restorers, preserving agents, and mixtures thereof. A person skilled in the art will take care to select the optional additives and the amount thereof such that they do not harm the properties of the compositions of the present disclosure.

In various embodiments, the additives are generally present in an amount ranging up to about 40% by weight of active material relative to the total weight of the composition, such as up to about 30%, up to about 20%, up to about 15%, up to about 10%, up to about 5%, such as from about 0.01% to about 20%.

In some embodiments, the rinse-off compositions are free or substantially free of silicones. For example, the compositions may in some embodiments include less than about 3%, less than about 2%, less than about 1%, or less than about 0.5% of silicones. In other embodiments, the compositions comprise silicones, for example in an amount of from about 0.1% up to about 1%, such as up to about 2%, up to about 3%, up to about 4%, or up to about 5%. Non-limiting examples of silicones include amine-functionalized silicones (e.g., amodimethicone), dimethicone, bis-aminopropyl dimethicone, trimethyl silylamodimethicone, etc.

The rinse-off compositions according to the disclosure may be contained in a jar, a tube, a bottle optionally equipped with a pump, or any suitable package.

Methods of Use

According to various embodiments, the rinse-off compositions may be useful in methods of treating and/or caring for the skin, hair, and/or scalp. By way of example, when the rinse-off compositions are shampoo compositions or conditioning shampoo compositions, the compositions may be useful in methods of cleansing and/or conditioning the hair and/or scalp. When the rinse-off compositions are skin care or skin cleansing compositions, the compositions may be useful in methods of cleansing and/or caring for the skin.

The compositions according to the disclosure may be applied to the skin, hair, and/or scalp and subsequently rinsed off. For example, the skin, hair, and/or scalp may be washed or cleansed in a first step of applying the composition of the disclosure onto the skin, hair, and/or scalp, with an optional leave-on time, followed by a second step of rinsing the hair with water, for example after an optional leave-on time, for example up to 10 minutes, up to 5 minutes, up to 2 minutes, up to 1 minute, up to 30 seconds, up to 20 seconds, up to 10 seconds, up to 5 seconds, etc.

The methods of treating and/or caring for the skin, hair, and/or scalp according to the disclosure may, in various embodiments, impart moisture benefits to the skin, or conditioning and manageability benefits to the hair, even after the composition is rinsed off. In addition, hair treated with the conditioning systems and/or rinse-off hair compositions according to the disclosure may, in certain exemplary embodiments, have greater ease of detangling, greater smoothness, discipline without a greasy coating or weighed-down feeling, moisturized feel, split-end seal, and/or reduced static, may be more sleek, and/or may have greater frizz control, relative to hair not having been treated with a composition according to the disclosure.

It should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

The compositions described throughout this disclosure may be rinse-off compositions. A "rinse-off" (also called rinse-out) product refers to a composition that is applied to the skin, hair, and/or scalp and subsequently rinsed, optionally after a period of time, such as after about 5 seconds, after about 10 seconds, after about 20 seconds, after about 30 seconds, after about 1 minute, after about 5 minutes, after about 10 minutes, after about 20 minutes, after about 30 minutes, or after about an hour.

As used herein, the term "keratinous substrate" is intended to include skin and hair.

As used herein, the terms "comprising," "having," and "including" are used in their open, non-limiting sense.

The terms "a," "an," and "the" are understood to encompass the plural as well as the singular. Thus, the term "a surfactant" includes both a single surfactant and a plurality of surfactants.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5%, 4%, 3%, 2%, or 1% of the indicated number. Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All percentages, parts and ratios herein are relative to the amount of active agent, based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

As used herein, the terms "free" and "substantially free" are intended to denote that the component is absent entirely from the composition, or is present in an amount considered by those skilled in the art to not provide an effect on the composition. For example, the component may be present in an amount below the level of detection, or may be present in an amount less than 3%, less than 2%, less than 1%, less than 0.5%, less than 0.1%, less than 0.01%, or less than 0.001%.

It should also be understood that the precise numerical values used in the specification and claims form additional embodiments of the disclosure, and are intended to include any ranges which may be narrowed to any two end points disclosed within the exemplary ranges and values provided, as well as the specific end points themselves. Efforts have been made to ensure the accuracy of the numerical values disclosed herein. Any measured numerical value, however, can inherently contain certain errors resulting from the standard deviation found in its respective measuring technique.

The compositions and methods of the present disclosure can comprise, consist of, or consist essentially of the essential elements and limitations of the disclosure described herein, as well as any additional or optional ingredients, components, or limitations described herein or otherwise useful.

Unless otherwise expressly stated, it is in no way intended that any method set forth herein be construed as requiring that its steps be performed in a specific order. Accordingly, where a method claim does not expressly recite that a particular order of steps must be followed or it is not otherwise specifically stated in the claims or descriptions that the steps are to be limited to a specific order, it is no way intended that any particular order be inferred.

All patents and publications are expressly incorporated herein in their entireties.

EXAMPLES

The following examples serve to illustrate the embodiments of the disclosure without however exhibiting a limiting character. The Examples are intended to be non-restrictive and explanatory only, with the scope of the invention being defined by the claims. In these examples the amounts of the composition ingredients are given as weight percentages of active ingredients relative to the total weight of the composition.

Examples 1A-1B—Rinse-Off Conditioning Shampoo

Two separate rinse-off shampoo compositions according to the disclosure were prepared by mixing the following ingredients in Table 1, as follows. First, the sodium cocoyl isethionate, water, polyquarternium compounds, PEG-150 distearate, and carbomer were mixed and heated to about 70°

C. As the mixture was cooling to room temperature, the remaining components were added and the composition was mixed until uniform.

TABLE 1

| US INCI NAME | EXAMPLE 1A | EXAMPLE 1B |
| --- | --- | --- |
| GLYCOL DISTEARATE | 0.105 | 0.12 |
| COCO-GLUCOSIDE | 11.44 | — |
| SODIUM COCOYL ISETHIONATE | 11 | 11 |
| COCAMIDOPROPYL BETAINE | 2.584 | 2.584 |
| COCO-BETAINE | 0.021 | 0.024 |
| POLYQUATERNIUM-10 | 0.11 | — |
| POLYQUATERNIUM-67 | 0.2 | 0.2 |
| SODIUM CHLORIDE | 0.68055 | 0.4812 |
| PEG-55 PROPYLENE GLYCOL OLEATE | 0.4 | 0.4 |
| PEG-150 DISTEARATE | 1 | 0.5 |
| COCO-CAPRYLATE/CAPRATE | 0.38 | 0.2 |
| TRIDECETH-6 and/or PPG-5-CETETH 20 | — | 0.215 |
| CETRIMONIUM CHLORIDE | — | 0.003 |
| DECYL GLUCOSIDE | — | 11.66 |
| GLYCERIN/PROPYLENE GLYCOL | — | 0.75 |
| DIMETHICONE | — | 0.75 |
| AMODIMETHICONE | — | 0.171 |
| CARBOMER and/or ACRYLATES/BEHENETH-25 METHACRYLATE COPOLYMER | — | 0.271 |
| ADDITIONAL COMPONENTS (pH adjuster, vitamins, etc.) | 1.610 | 2.910 |
| WATER | QS | QS |
| PH | 6.0 | 5.7 |

The cosmetic properties of compositions 1A and 1B, which comprise the conditioning system described herein, were evaluated. The compositions were found to have dense, lush, creamy foam, with a viscosity that would be typical of a shampoo composition. This was surprising because generally the inclusion of esters would be expected to negatively affect these cosmetic properties of the shampoo composition. Thus, the components of the conditioning system synergistically worked together in order to avoid such a negative effect on the composition properties.

Compositions 1A and 1B were then applied to wet hair, lathered, and the hair was rinsed, combed, dried, and styled. The compositions lathered very well and coated the hair nicely. The compositions rinsed easily from the hair. After rinsing, the ease of detangling the wet hair was superior.

After the hair was dried and styled, the hair had excellent properties of shine and frizz control, felt moisturized but not greasy, had good manageability, shaping, and discipline (e.g. no "fly-aways"), and had smooth ends.

The above example demonstrates that the synergistic combination of isethionate surfactant, coco-caprylate/caprate, and polysaccharide-based cationic compound provide unexpectedly superior cosmetic properties to the rinse-off composition, as well as unexpectedly superior cleansing and conditioning properties which leave the hair in surprisingly excellent condition.

The invention claimed is:

1. A rinse-off composition comprising:
(a) an anionic surfactant system comprising:
  i) a first anionic surfactant chosen from isethionate surfactants, and
  ii) optionally, a second anionic surfactant;
(b) coco-caprylate/caprate;
(c) at least one cationic compound;
(d) at least one additional surfactant chosen from nonionic and amphoteric surfactants; and
(e) water;

wherein the coco-caprylate/caprate is present in the rinse-off composition in an amount ranging from about 0.05% to about 3% by weight, relative to the total weight of the rinse-off composition.

2. The rinse-off composition of claim 1, wherein the at least one first anionic surfactant is chosen from acyl isethionates of formula (I):

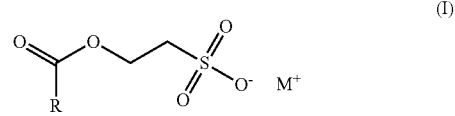

wherein:
R is chosen from H or an alkyl chain having from 1 to 30 carbon atoms, and
$M^+$ is an alkali metal ion.

3. The rinse-off composition of claim 1, wherein the at least one first anionic surfactant is chosen from sodium cocoyl isethionate, sodium lauroyl isethionate, or a mixture thereof.

4. The rinse-off composition of claim 1, wherein the at least one first anionic surfactant is present in the composition in an amount ranging from about 4% to about 15% by weight, relative to the total weight of the rinse-off composition.

5. The rinse-off composition of claim 1, wherein the anionic surfactant system is present in the composition in an amount ranging from about 5% to about 25% by weight, relative to the total weight of the rinse-off composition.

6. The rinse-off composition of claim 1, wherein the at least one cationic compound is chosen from cationic polysaccharide-based cationic compounds, cationic silicone compounds, or a mixture thereof.

7. The rinse-off composition of claim 6, wherein the polysaccharide-based cationic compounds are chosen from cationic cellulose-based compounds, cationic starch-based compounds, cationic guar-based compounds, or a mixture thereof.

8. The rinse-off composition of claim 6, wherein the cationic silicone compounds are chosen from amino silicones.

9. The rinse-off composition of claim 1, wherein the at least one cationic compound is present in an amount ranging from about 0.001% to about 5% by weight, relative to the total weight of the rinse-off composition.

10. The rinse-off composition of claim 1, wherein the at least one additional surfactant is chosen from alkyl polyglucosides.

11. The rinse-off composition of claim 10, wherein the at least one alkyl polyglucoside is chosen from compounds of formula (XIII):

wherein:
$R^1$ is an alkyl group having from 8 to 18 carbon atoms;
$R^2$ is an ethylene or propylene group;
Z is a saccharide group with 5 to 6 carbon atoms;
n is an integer from 0 to 10; and
x is an integer from 1 to 5.

12. The rinse-off composition of claim 10, wherein the at least one alkyl polyglucoside is present in the composition in an amount ranging from about 0.01% to about 15% by weight, relative to the total weight of the rinse-off hair composition.

13. The rinse-off composition of claim 1, wherein the at least one additional surfactant is chosen from amphoteric surfactants.

14. The rinse-off composition of claim 13, wherein the at least one amphoteric surfactant is chosen from betaines, sultaines, amphoacetates, amphoproprionates, or a mixture thereof.

15. The rinse-off composition of claim 13, wherein the at least one amphoteric surfactant is present in the composition in an amount ranging from about 0.001% to about 10% by weight, relative to the total weight of the rinse-off composition.

16. A rinse-off composition comprising:
(a) an anionic surfactant system comprising:
  i) from about 4% to about 15% by weight, relative to the total weight of the rinse-off composition, of a first anionic surfactant chosen from sodium cocoyl isethionate, sodium lauroyl isethionate, or a mixture thereof, and
  ii) at least one second anionic surfactant;
(b) from about 0.01% to about 5% by weight, relative to the total weight of the rinse-off composition, of coco-caprylate/caprate;
(c) at least one cationic compound chosen from at least one polysaccharide-based cationic compound, at least one cationic silicone compound, or a mixture thereof;
(d) from about 7% to about 15% by weight, relative to the total weight of the rinse-off composition, of at least one alkypolyglucoside;
(e) from about 0.01% to about 7% by weight, relative to the total weight of the rinse-off composition, of at least one amphoteric surfactant; and
(f) water.

17. A conditioning system comprising:
(a) at least one anionic surfactant chosen from isethionate surfactants, present in an amount ranging from about 90% to about 99% by weight, relative to the total weight of the conditioning system;
(b) coco-caprylate/caprate, present in an amount ranging from about 0.05% to about 3% by weight, relative to the total weight of the conditioning system; and
(c) at least one cationic compound, present in an amount ranging from about 0.5% to about 5% by weight, relative to the total weight of the conditioning system.

18. The conditioning system of claim 17, comprising:
(a) from about 93% to about 97% by weight, relative to the total weight of the conditioning system, of at least one anionic surfactant chosen from acyl isethionates of formula (I):

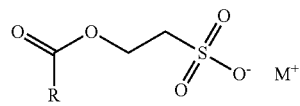

wherein:
  R is chosen from H or an alkyl chain having from 1 to 30 carbon atoms, and
  $M^+$ is an alkali metal ion;
(b) from about 1.5% to about 3.5% by weight, relative to the total weight of the conditioning system, of coco-caprylate/caprate; and
(c) from about 1.5% to about 3.5% by weight, relative to the total weight of the conditioning system, of at least one cationic compound chosen from cationic cellulose derivatives, cationic guar gum derivatives, or a mixture thereof.

19. A method for cleansing the skin, hair, and/or scalp, said method comprising applying to the skin, hair, and/or scalp a composition comprising:
(a) an anionic surfactant system comprising:
  i) a first anionic surfactant chosen from isethionate surfactants, and
  ii) optionally, a second anionic surfactant;
(b) coco-caprylate/caprate;
(c) at least one cationic compound;
(d) at least one additional surfactant chosen from nonionic and amphoteric surfactants; and
(e) water;
wherein the coco-caprylate/caprate is present in the rinse-off composition in an amount ranging from about 0.05% to about 3% by weight, relative to the total weight of the rinse-off composition.

20. The rinse-off composition of claim 1, comprising:
(a) from about 10% to about 15% of sodium cocoyl isethionate;
(b) from about 0.1% to about 1% of coco-caprylate/caprate;
(c) at least one cationic cellulose derivative;
(d) at least one amphoteric surfactant chosen from cocobetaine, cocamidopropylbetaine, and mixtures thereof; and
(e) water.

* * * * *